United States Patent [19]
Weiler et al.

[11] Patent Number: 5,347,997
[45] Date of Patent: Sep. 20, 1994

[54] CURVED GUIDING OF A LITHOTRIPSY HEAD

[75] Inventors: Herbert Weiler, Alling, Fed. Rep. of Germany; Ulrich Hagelauer, Bottighofen, Switzerland; Michael Weingart, Munich, Fed. Rep. of Germany

[73] Assignee: Dornier Medizintechnik GmbH, München, Fed. Rep. of Germany

[21] Appl. No.: 294,464

[22] Filed: Jan. 6, 1989

[30] Foreign Application Priority Data

Jan. 28, 1988 [DE] Fed. Rep. of Germany ... 8800986[U]

[51] Int. Cl.$^5$ .............................................. A61B 17/22
[52] U.S. Cl. ................................................... 601/3
[58] Field of Search .............................. 378/197, 198; 128/653.1, 24 EL, 660.03

[56] References Cited

U.S. PATENT DOCUMENTS

5,073,917 12/1991 Van Endschot et al. .......... 378/197
5,165,412 11/1992 Okazaki ........................... 128/24 EL

*Primary Examiner*—Ruth S. Smith

[57] ABSTRACT

Guiding for a therapeutic head for a medical shock wave generator includes a curved rail and a support for a plurality of rollers; the rail is provided with a plurality of grooves, and stainless steel wires are inserted in these grooves and project therefrom to serve as tracks in that the rollers run on the wires; in one version (FIG. 2, 3) the therapeutic head is mounted to the rail while the roller support is stationary; in an alternate version (FIG. 4) the relation is reversed.

4 Claims, 2 Drawing Sheets

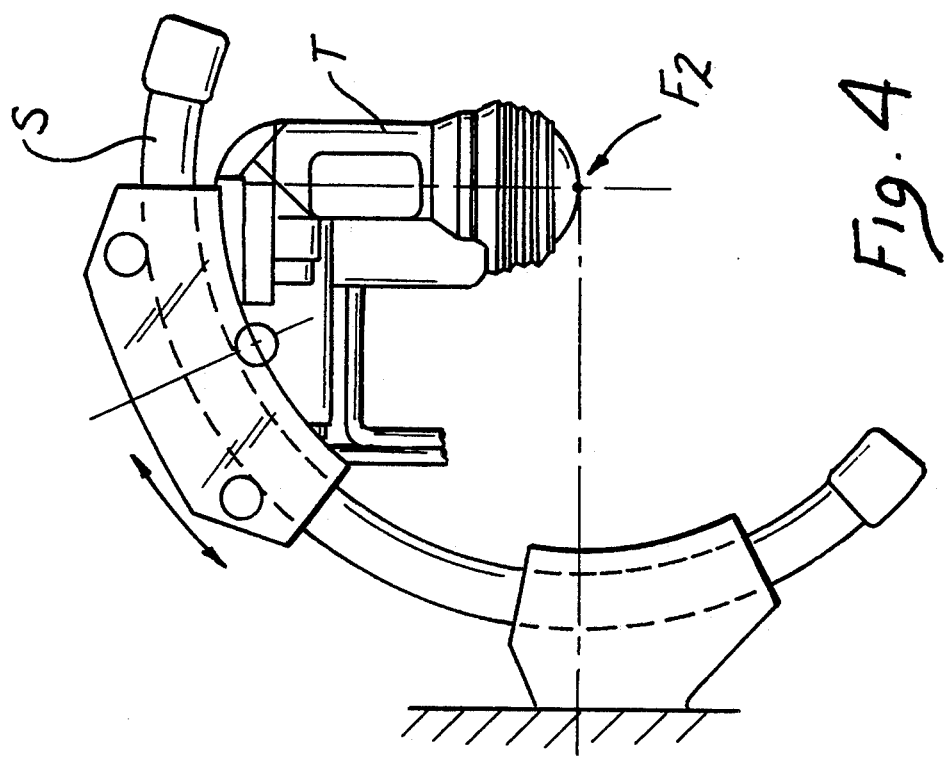
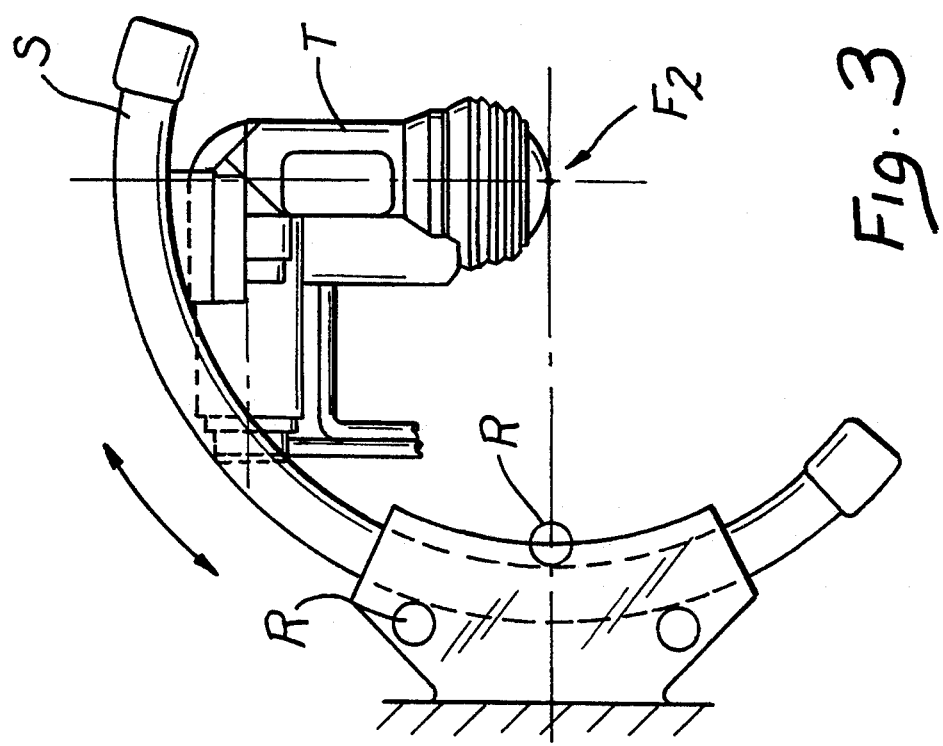

CURVED GUIDING OF A LITHOTRIPSY HEAD

BACKGROUND OF THE INVENTION

The present invention relates to the guiding of a therapeutic head of a shock wave device preferably a lithotripter under utilization of rails and rollers.

Apparatus for the extracorporeal i.e. noninvasive lithotripsy for the purposes of comminuting gall stones or kidney stones, include equipment and devices for the production of high energetic, pressure pulses such as shock waves. These shock waves are produced outside of the body of the patient and are focused to actually converge in a focal point that is located within the particular stone or concrement. Devices of this kind are shown in German Patent 34 27 001 corresponding to U.S. Pat. No. 4,669,483. Broad reference is also made to a paper "Extracorporeal shock wave lithotripsy" by Chaussy (editor) 1982 which gives a good background of the particular arrangement. The particular new development lead to the device shown in the above mentioned German patent and the corresponding to U.S. Pat. No. 4,669,483. Here an ultrasonic therapeutic head is supported by means of a C-shaped rail to be freely movable in relation to the body of the patient so as to be positionable with as few restraints as possible.

A copending application Ser. No. 07/294,472 filed Jan. 6, 1989 describes a device by means of which the shock wave generator system is moved around a stone vis-a-vis the therapeutic focus. The resulting isocentric movement is produced by means of a superimposing transmission which is provided with a rotational axis and an eccentrically displaced semi-circular crack. The vertical on the center of the circle as far as the track is concerned intersect in the focal point. Further to the state of the relevant and related art, reference is made to U.S. Pat. No. 4,705,026.

DESCRIPTION OF THE INVENTION

It is an object of the present invention to provide a new and improved guiding system relating to the running and guiding of a therapeutic shock wave generating head.

In accordance with the preferred embodiment of the present invention, it is suggested to provide a curved rail with grooves and to insert track defining wires into these grooves and rollers run on these wires. Either the rollers are stationarily mounted with the curved rail being moved, the therapeutic head then being affixed so that rail, or the curved rail is stationary and the therapeutic head is mounted on a carriage that runs on these track defining wires in the rail.

The rail is preferably of rectangular or square shaped cross section and the wires are arranged in pairs whereby the wires of one pair are arranged near the corners of one side of the rail and the wires of the other pair are correspondingly arranged on the opposite side of the rail. The wires are preferably of circular cross section made of a particular stainless steel.

DESCRIPTION OF THE DRAWINGS

While the specification concludes with claims particularly pointing out and distinctly claiming the subject matter which is regarded as the invention, it is believed that the invention, the objects and features of the invention, and further objects, features and advantages thereof will be better understood from the following description taken in connection with the accompanying drawings in which:

FIG. 3 is a modified drive system for the arrangement shown in FIG. 2; and

FIG. 4 is a side view of a dynamic inversion of the system shown in FIG. 3.

Figure 2:
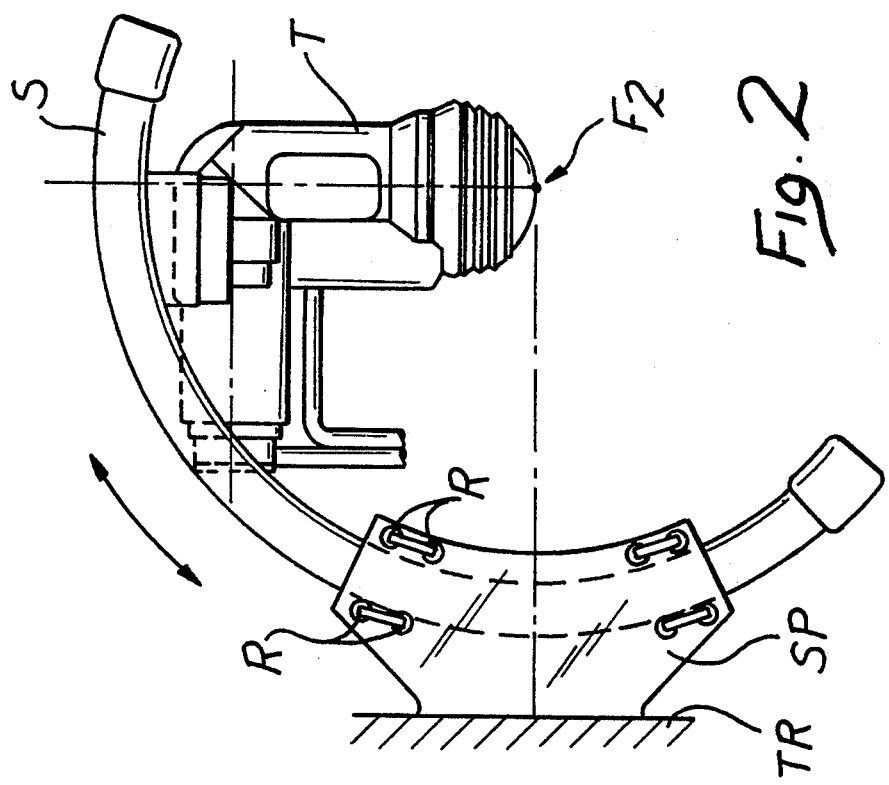
FIG. 2 illustrates a side view of a rail system using the rail structure shown in FIG. 1 and showing a therapeutic head as used in lithotripsy being guided on this rail system.
Figure 1:
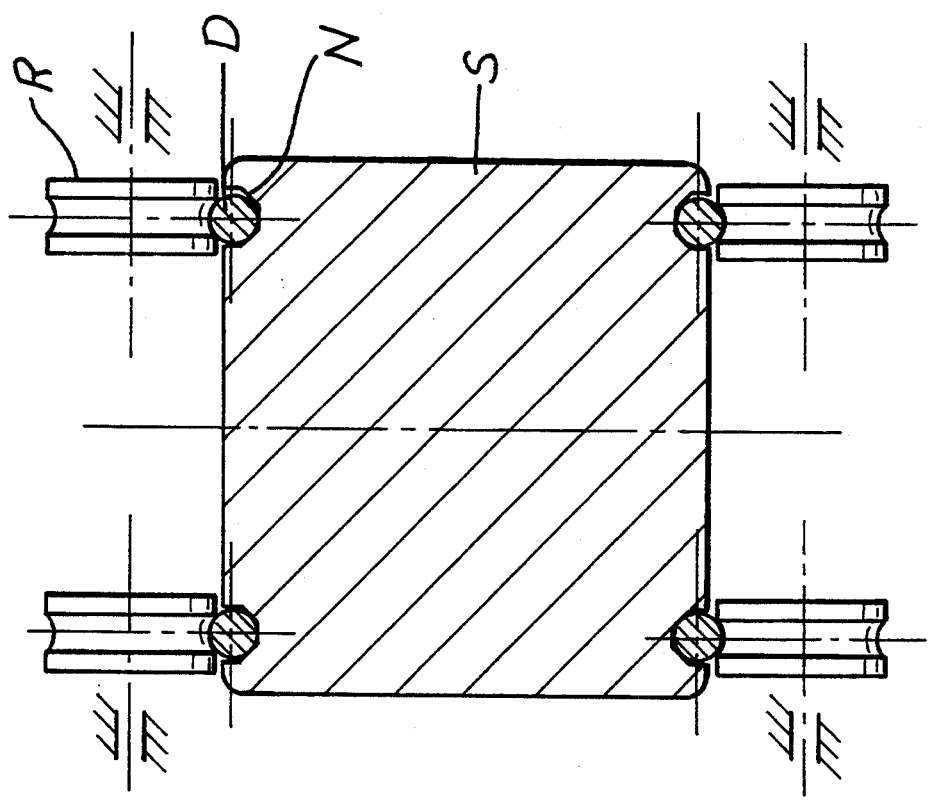
FIG. 1 is a cross section through a guide and rail structure in accordance with the preferred embodiment of the present invention for practicing the best mode thereof.

Proceeding now to the detailed description of the drawings, FIG. 1 and the others illustrate a rail which as shown in FIG. 2, 3 and 4 is of a curved configuration covering almost half a circle but the angular extension is not essential in principle. The rails as shown in FIG. 1 has a near square shaped, rectangular cross section and there are four grooves N cut into the rail S. The grooves are arranged in pairs as shown, and on opposite faces as far as the basic extension of the rail is concerned. The grooves are of semi-octogonal cross section.

Each of the grooves receives a wire D which extends over the length of the groove in each instance, but projects somewhat beyond to permit appropriate fastening. These wires are tensioned and thus held taut in the outside curved grooves. The inside track wires in the concave surface of rails may be held in the respective grooves by solder spots or the like.

The wires constitute the track proper for individual rollers R which are arranged to run on these wires, the rollers have peripherally arranged grooves G to engage the wires over a nonline shaped surface portion of the respective periphery. The arrangement is dynamically suitable for either of two modes of operations. In one instance it is possible to provide the rollers R in stationary journals and the rail S will then move along the circular path defined by its own curved configuration (FIG. 2 and 3). Alternatively the rail S may be held stationary and a carriage-like arrangement having these rollers R, equivalent to vehicles wheels run on the wires D as the rail moves (FIG. 4). The therapeutic head T is connected in each instance of course with the respective moving part.

In the example shown in FIGS. 2 and 3 it is assumed that the rollers R are journaled in stationary support structure SP retaining a support post or tower TR. A lithotriptic therapeutic head T is fixed, from an overall point of view, to the rail S and moves therewith. The head includes the fastening structure TS and may by and in itself be movable on axes X and Y. Moreover as can be seen in FIGS. 2 and 3 the movement is such that a particular portion of the head T coincides with the center F2 of the curved rail S and remains invariant as the rail S moves within the roller assembly R-SP.

Turning to further particulars of FIG. 2 as stated there is to the left a stationary carrier or tower TR to which are connected bracket elements or the like, SP constituting the basic support in which the rollers R are arranged and in a plurality of pairs; there are illustrated at least altogether eight rollers R, and another set of rollers is in a plane parallel to the plane of the drawing of FIG. 2. The therapeutic head T is fixedly mounted as a whole to the rail S through the mount and fastening structure TS.

The double arrow denotes the movement and, as stated, the movement is such that the point F2 remains invariant. In other words, rail S and head T move about this point F2, F2 may e.g. be a focal point into which the therapeutic unit T focuses shock waves generated in its interior. In other words the equipment as shown varies the direction of the therapeutic equipment T vis-a-vis the focal point F2 being a point which may (and at times will) coincide with a kidney stone or the like but the distance from F2 is not changed by this equipment as it moves along the curved face.

The number of rollers is relatively limited. There are only sixteen in this case, and they are capable of retaining lateral forces. It is important that the support is statically determined in a definite fashion. The foregoing result obtains in that four of the rollers are, so to speak, fixed as to their journal and the four others are mounted in slidable bearings. FIG. 2 shows the rollers such that the ones on the left hand side run so to speak on the outside curve of the track and rail S and they are fixed in terms of bearings while the bearing mount for the other four rollers running on the inside is resiliently biased. The same is true for the other rollers in the aforementioned plane parallel to the plane shown in FIG. 2.

The wires D are fairly simple semi-finished wires and have to satisfy only fairly limited tolerance requirements as far as the manufacture of the total track arrangement is concerned. The wires D however as well as the rollers R are to be made of high quality material in order to obtain favorable surface and strength properties. A compound configuration seems to be preferred. As far as material is concerned, it is practical to use for the rollers the kind of steel used in ball bearings. Such rollers can be bought from a company called INA in Nuernberg, Fed. Republic of Germany. The wires are highly alloyed, hardenable stainless steel e.g. of the type known under the designation $X_{40}Cr_{13}$. The surface of the particular element, be it a roller or wire, can be made as follows. The wires D may be inserted in that the groove as stated which establish fairly easily cleanable and optically pleasing configuration.

The invention described was referenced to a rectangular rail body but others configurations may be advisable or suitable in different fields of application. The number of wires also depends on the circumstances. However, the present configuration is deemed to be the best mode in lithotripsy. By way of an alternative example a rail body may have a round surface with longitudinal grooves more or less regularly distributed around the periphery. There may be three, four or five such grooves being established to receive a corresponding number of wires.

Inside and outside a track portion of the rails may not necessarily have the same number of rollers. The same number of rollers are shown in FIG. 2 but there is no essentiality in principle involved. FIG. 3 illustrates a modified version, the example simply shows that the rollers R here are larger and the number is smaller. A single (pair of) roller is situated on the inside and two roller pairs are on the outside. The respective other one of each pair is respectively behind the drawing.

FIG. 4 illustrates the dynamic inversion. Three roller pairs are mounted here on a carriage C to which the head T (fastening portion TS) is connected. The rail S is held in a stationary bracket BR that extends from tower TR.

The term roller is to be understood more generally as a roller is in effect a drum shaped element of relatively short axial dimensions, the axial dimensions can be longer if such is deemed practical.

The invention is not limited to the embodiments described above but all changes and modifications thereof, not constituting departures from the spirit and scope of the invention, are intended to be included.

We claim:

1. Medical treatments apparatus including a therapeutic head which includes a shockwave generator, further including structure for guiding the therapeutic head and the medical shockwave generator therein, the guiding structure comprising:
    a curved rail element;
    support means for the plurality of rollers;
    said rail element being provided with a plurality of grooves;
    wires respectively inserted in said grooves and projecting therefrom for serving as a rail track, said rollers running on said wires; and
    said therapeutic head being mounted to one of (i) the roller support means and (ii) the rail element, the respective other one being stationarily mounted and fixed.

2. Medical treatment apparatus in accordance with claim 1, said curved rail element having a surface on an inside of curving and an outside surface with respect to the curving of the rail element, each of the surfaces having two of said grooves, each said groove receiving one of said wires.

3. Medical treatment apparatus in accordance with claim 1, each of said wires having circular cross section.

4. Medical treatment apparatus in accordance with claim 1, said wires being stainless steel wires.

* * * * *